US008435643B2

(12) United States Patent
Warburton et al.

(10) Patent No.: US 8,435,643 B2

(45) Date of Patent: May 7, 2013

(54) ANTISAPSTAIN COMPOSITIONS COMPRISING A HALOALKYNL COMPOUND, AN AZOLE AND AN UNSATURATED ACID

(75) Inventors: Paul Stuart Warburton, Normanton (GB); Lee Mason, Selby (GB); Andrew Stewart Hughes, Pontefraut (GB)

(73) Assignee: Arch Timber Protection Limited, Castleford, West Yorkshire (GB)

( * ) Notice: Subject to any disclaimer, the term of this patent is extended or adjusted under 35 U.S.C. 154(b) by 0 days.

(21) Appl. No.: 12/925,730

(22) Filed: Oct. 28, 2010

(65) Prior Publication Data

US 2011/0111245 A1 May 12, 2011

Related U.S. Application Data

(63) Continuation of application No. PCT/GB2009/001104, filed on Apr. 30, 2009.

(30) Foreign Application Priority Data

Apr. 30, 2008 (GB) .................................. 0807905.5

(51) Int. Cl.
*B32B 21/04* (2006.01)

(52) U.S. Cl.
USPC ........ 428/537.1; 428/536; 514/242; 514/383; 514/479; 514/483; 514/549; 424/405

(58) Field of Classification Search ............... 428/537.1, 428/536; 514/242, 383, 479, 483, 549; 424/405
See application file for complete search history.

(56) References Cited

U.S. PATENT DOCUMENTS

| | | | | |
|---|---|---|---|---|
| 3,923,870 | A | 12/1975 | Singer | |
| 4,259,350 | A | 3/1981 | Morisawa et al. | |
| 4,592,773 | A | 6/1986 | Tanaka et al. | |
| 4,616,004 | A | 10/1986 | Edwards et al. | |
| 4,719,227 | A | 1/1988 | Schade et al. | |
| 4,945,109 | A | 7/1990 | Raydu | |
| 5,059,629 | A * | 10/1991 | Patton et al. | 521/84.1 |
| 5,196,407 | A | 3/1993 | Goletz et al. | |
| 5,200,421 | A | 4/1993 | Ludwig et al. | |
| 5,399,190 | A | 3/1995 | Conradie et al. | |
| 5,880,143 | A | 3/1999 | Goettsche et al. | |
| 7,056,919 | B2 * | 6/2006 | Ross et al. | 514/242 |
| 7,655,281 | B2 * | 2/2010 | Ward et al. | 427/440 |
| 2004/0258768 | A1 * | 12/2004 | Richardson et al. | 424/630 |
| 2009/0215845 | A1 | 8/2009 | Bruns et al. | |

FOREIGN PATENT DOCUMENTS

| | | |
|---|---|---|
| EP | 0393746 | 10/1990 |
| GB | 2438404 | 11/2007 |
| JP | 2005/047056 | 2/2005 |
| WO | 02/069716 | 9/2002 |
| WO | 03/104583 | 12/2003 |
| WO | 2006/072659 | 7/2006 |
| WO | 2007/026008 | 3/2007 |
| WO | 2007/092580 | 8/2007 |
| WO | 2007/109735 | 9/2007 |
| WO | 2007/135435 | 11/2007 |

* cited by examiner

*Primary Examiner* — Leszek Kiliman

(74) *Attorney, Agent, or Firm* — Lucas & Mercanti LLP

(57) ABSTRACT

The present invention provides antisapstain compositions comprising a haloalkynyl compound, an azole and an unsaturated carboxylic or sulphonic acid. The compositions of the invention are surprisingly effective at protecting wood and other cellulosic substrates, in particular at providing antisapstain activity. The invention also provides methods for treating wood and other cellulosic substrates with said compositions.

20 Claims, 5 Drawing Sheets
(4 of 5 Drawing Sheet(s) Filed in Color)

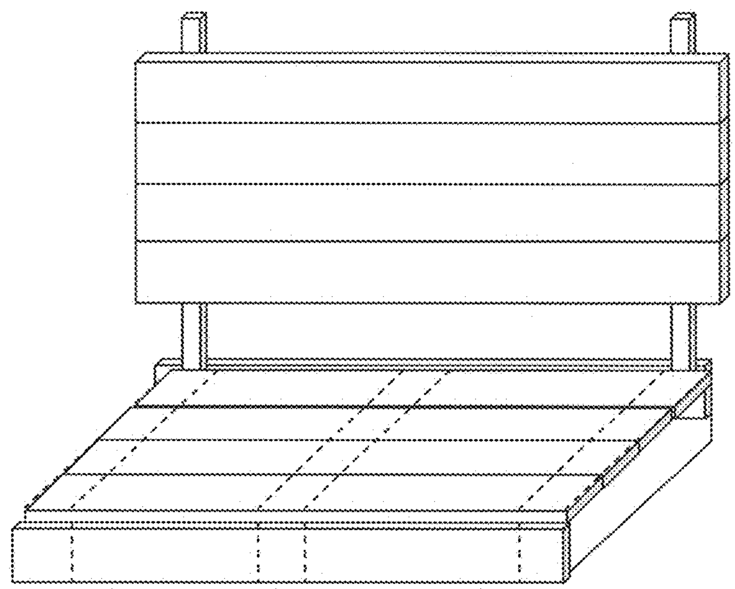
Figure 1: Decking/Cladding assembly built for natural weathering exposure

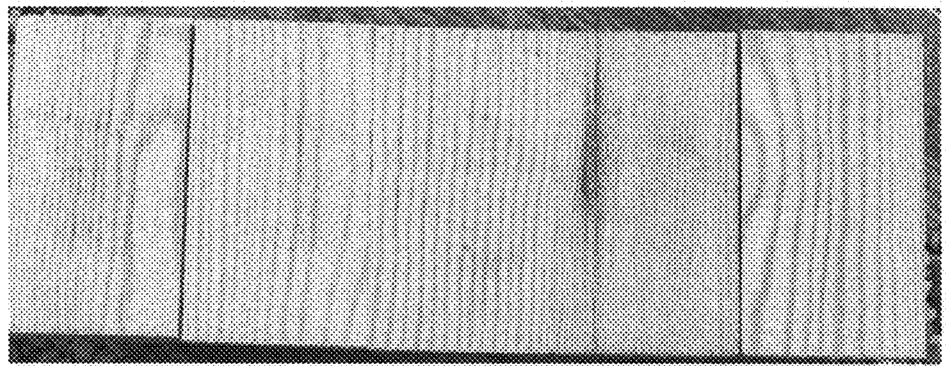
Figure 2: Wood treated with Formulation II-2 (IPBC + sodium benzoate) after exposure for 25 weeks
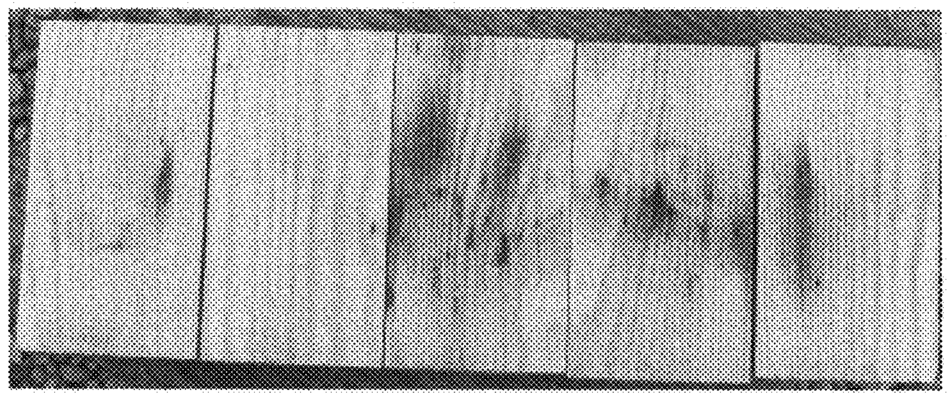
Figure 3: Wood treated with Formulation II-14 (tebuconazole/propiconazole + sodium benzoate) after exposure for 25 weeks.
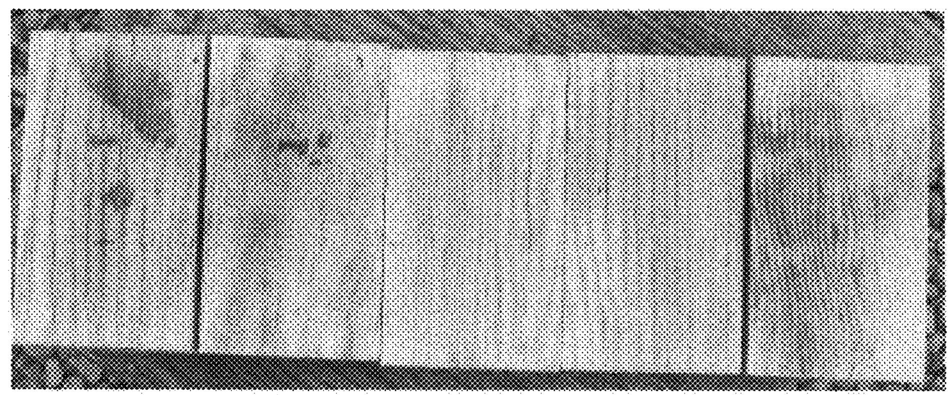
Figure 4: Wood treated with Formulation II-19 (IPBC + tebuconazole/propiconazole) after exposure for 25 weeks.

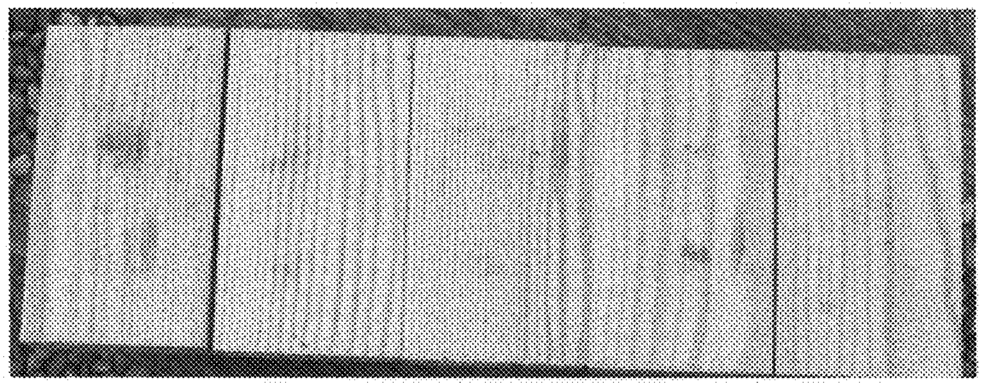
Figure 5: Wood treated with Formulation II-24
(IPBC + tebuconazole/propiconazole + sodium benzoate)
after exposure for 25 weeks.
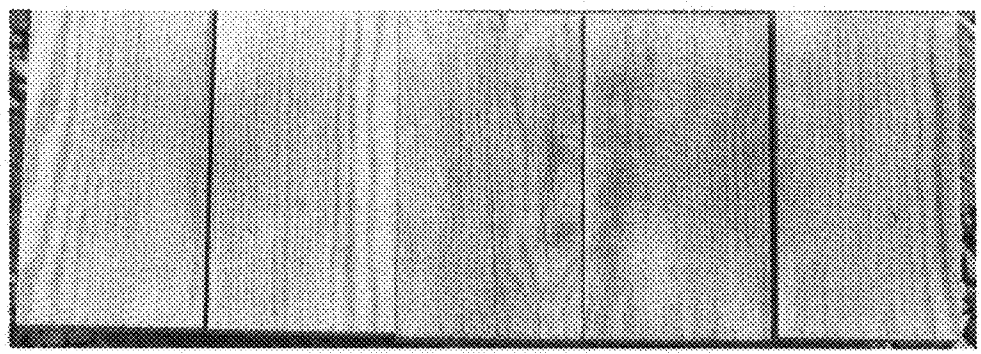
Figure 6: Wood treated with Formulation II-1 (IPBC)
after exposure for 25 weeks.
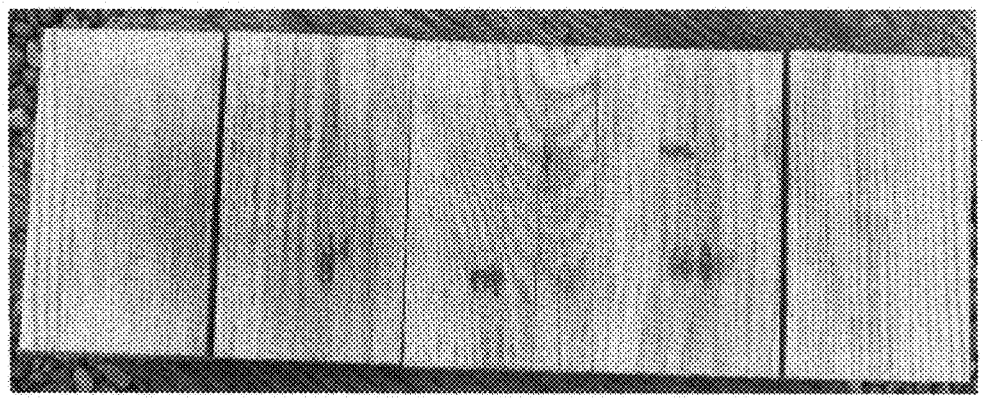
Figure 7: Wood treated with Formulation II-16 (IPBC + propiconazole)
after exposure for 25 weeks.

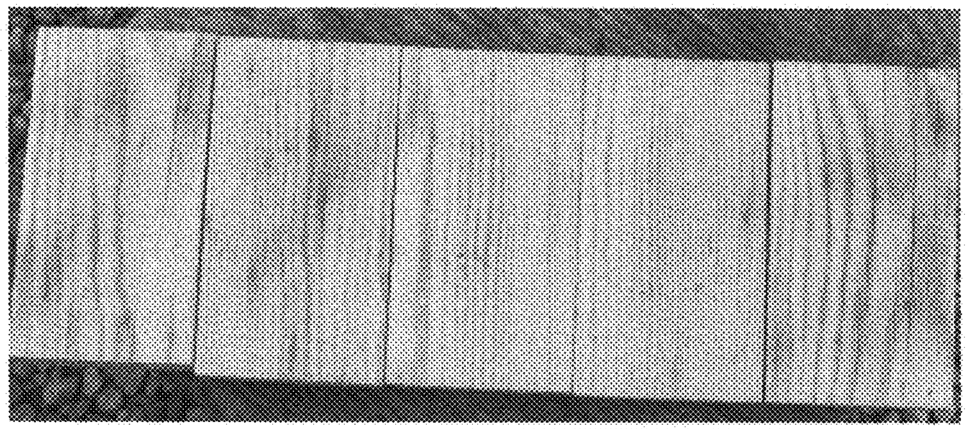
Figure 8: Wood treated with Formulation II-27 (IPBC + propiconazole + abietic acid) after exposure for 25 weeks.
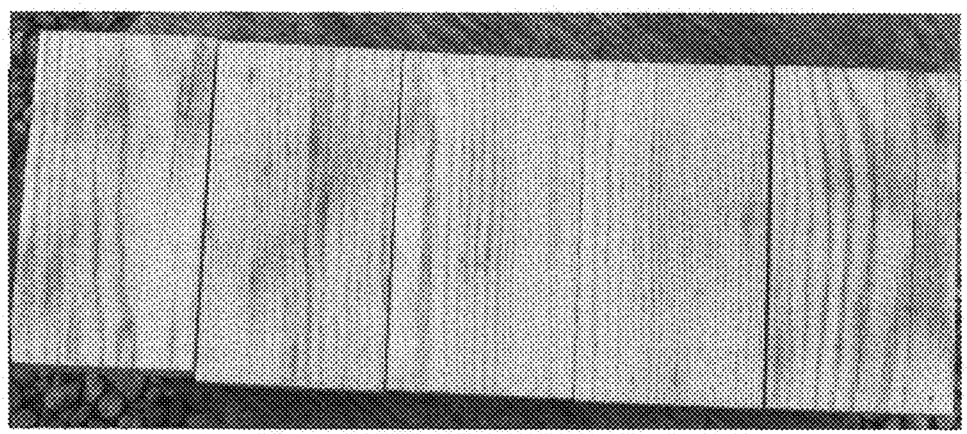
Figure 9: Wood treated with Formulation II-32 (IPBC + tebuconazole/propiconazole +sodium salicyclate) after exposure for 25 weeks.
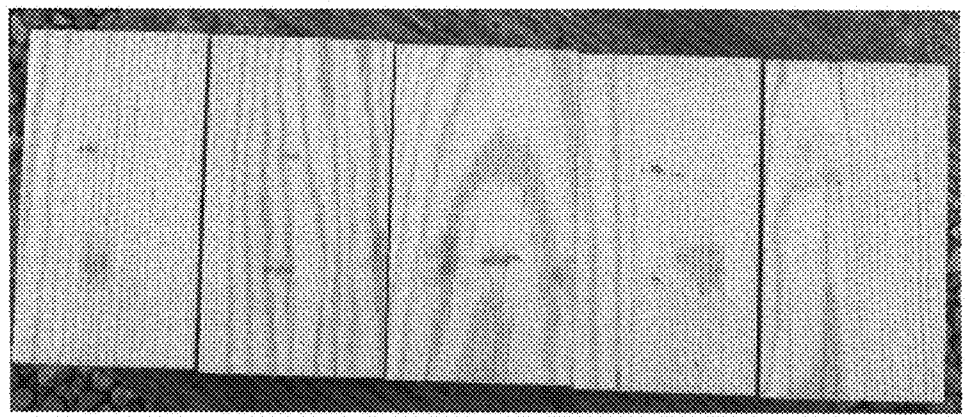
Figure 10: Wood treated with Formulation II-33 (IPBC + tebuconazole/propiconazole + potassium sorbate) after exposure for 25 weeks.

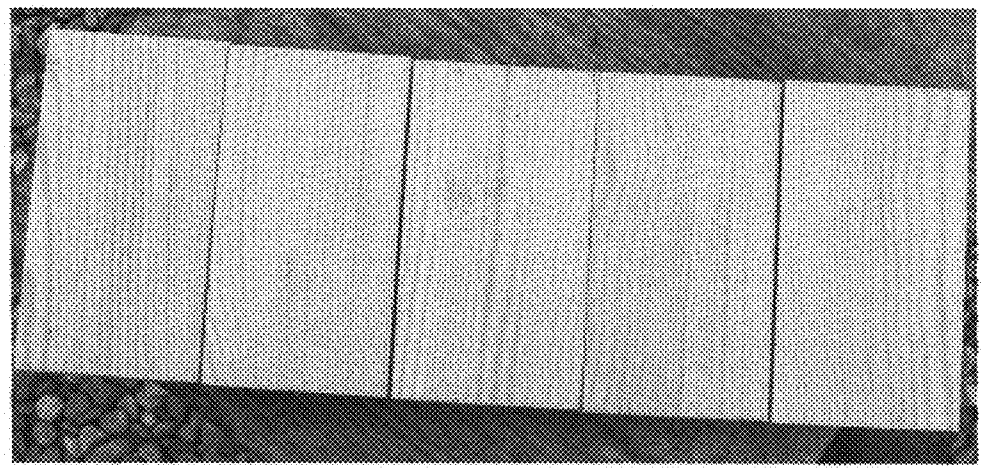
Figure 11: Wood treated with Formulation II-34 (IPBC + tebuconazole/propiconazole + rosin) after exposure for 25 weeks.
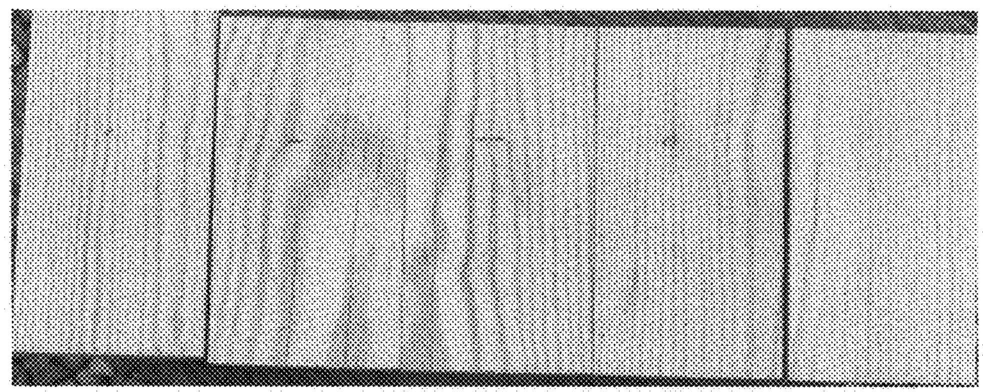
Figure 12: Wood treated with Formulation II-35 (IPBC + tebuconazole/propiconazole + sorbic acid) after exposure for 25 weeks.
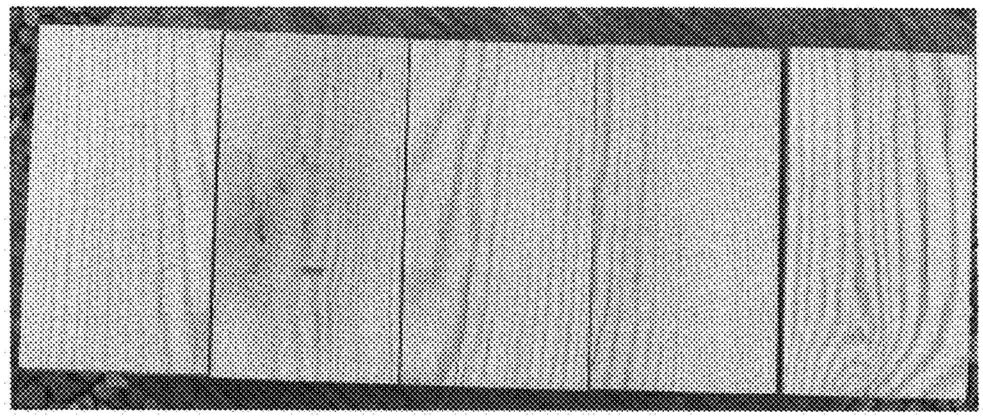
Figure 13: Wood treated with Formulation II-36 (IPBC + tebuconazole/propiconazole + oleic acid) after exposure for 25 weeks.

ANTISAPSTAIN COMPOSITIONS COMPRISING A HALOALKYNL COMPOUND, AN AZOLE AND AN UNSATURATED ACID

CROSS-REFERENCE TO RELATED APPLICATIONS

This application is a continuation application of PCT/GB2009/001104 filed Apr. 30, 2009, which claims the benefit of GB 0807905.5 filed Apr. 30, 2008. The disclosures of PCT/GB2009/001104 and GB 0807905.5 are incorporated herein by reference in their entireties.

The present invention relates to formulations for protecting wood and other cellulosic substrates against moulds, staining and other defacing organisms, and in particular to antisapstain applications.

Antisapstain chemicals are used to protect timber, in particular freshly felled or sawn timber, from attack by moulds, sapstain and decay fungi which would otherwise discolour the timber and so reduce its value.

A commonly used chemical in anti-sapstain applications is 3-iodo-2-propynyl-butyl-carbamate (IPBC). However, IPBC is known to be susceptible to degradation by a number of mechanisms, all of which compromise its performance against mould and stain. Known mechanisms by which IPBC can be rendered inactive are decomposition by exposure to UV, by bacteria, by hydrolysis and by reaction with metal ions. Exposure to UV can be problematic as treated timber is often stored outside in direct sunlight during common commercial practices. Furthermore, antisapstain compositions are typically applied by dipping processes using metal dipping tanks. Often, either the processing equipment used to dip the timber or the dipping tank itself suffer corrosion, allowing reactive metal ions to leach into the dipping solution. These metal ions can react with any IPBC present in the antisapstain solution, rendering it inactive.

The present inventors have found that the protection from mould and other staining organisms afforded by haloalkylnyl containing timber treatment formulations can be greatly enhanced by the inclusion of a number of unsaturated acids, salts or precursors thereof.

Thus, the present invention provides an antisapstain composition comprising a haloalkynyl compound, an azole and an unsaturated carboxylic or sulphonic acid, salt or precursor thereof.

The haloalkylnyl compounds used in the composition of the present invention are represented by the general formula (I):

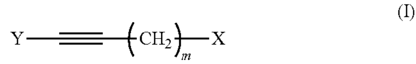

(I)

wherein Y is a halogen, preferably iodine;

m is an integer between 1 and 3;

and X can be (1) oxygen which is part of an organic functional group; 2) nitrogen which is part of an organic functional group; (3) sulphur which is part of an organic functional group; or (4) carbon which is part of an organic functional group.

The functional group of which oxygen is a part is preferably an ether, ester, or carbamate group. The functional group of which nitrogen is a part is preferably an amine, amide, urea, nitrile, or carbamate group. The functional group of which sulphur is a part is preferably a thiol, thiane, sulfone, or sulfoxide group. The organic functional group of which carbon is a part is preferably an ester, carbamate or alkyl group.

Examples of compounds which may be used as the haloalkynyl compound of this invention are especially the fungicidally active iodoalkynyl derivatives. Suitable iodoalkynyl derivates are disclosed in U.S. Pat. Nos. 3,923,870, 4,259,350, 4,592,773, 4,616,004, 4,719,227, and 4,945,109. These iodoalkynyl derivatives include compounds derived from propargyl or iodopropargyl alcohols such as the esters, ethers, acetals, carbamates and carbonates and the iodopropargyl derivatives of pyrimidines, thiazolinones, tetrazoles, triazinones, sulfamides, benzothiazoles, ammonium salts, carboxamides, hydroxamates, and ureas.

Thus, preferred haloalkynyl compounds include compounds of the general formula (II):

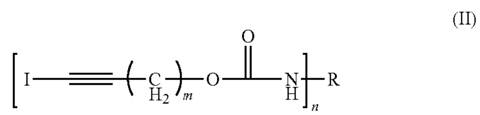

(II)

wherein R is selected from the group consisting of hydrogen, substituted and unsubstituted alkyl groups having from 1 to 20 carbon atoms, substituted and unsubstituted aryl, alkyl aryl, and aralkyl groups having from 6 to 20 carbon atoms and from substituted and unsubstituted cycloalkyl and cycloalkenyl groups of 3 to 10 carbon atoms, and m and n are independently integers from 1 to 3, i.e., m and n are not necessarily the same. Preferably, n is 1.

Preferably the haloalkynyl compound is an iodopropynyl carbamate. Preferred are compounds where m is 1 and n is 1 having the following formula (III):

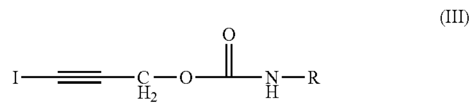

(III)

Suitable R substituents include alkyls such as methyl, ethyl, propyl, n-butyl, t-butyl, pentyl, hexyl, heptyl, octyl, nonyl, decyl, dodecyl, octadecyl, cycloalkyls such as cyclohexyl, aryls such as phenyl, alkaryls and aralkyls such as benzyl, tolyl, halogenated alkyls and aryls, such as chlorobutryl and chlorophenyl, and alkoxy aryls such as ethoxyphenyl and the like.

Especially preferred haloalkynyl compounds of this formula include iodopropynyl carbamates such as 3-iodo-2-propynyl propyl carbamate, 3-iodo-2-propynyl butyl carbamate, 3-iodo-2-propynyl hexyl carbamate, 3-iodo-2-propynyl cyclohexyl carbamate, 3-iodo-2-propynyl phenyl carbamate, and mixtures thereof. Most preferred is 3-iodo-2-propynyl butyl carbamate (IPBC).

By "unsaturated carboxylic acid" and "unsaturated sulphonic acid" is meant any carboxylic or sulphonic acid that also contains a carbon-carbon double bond. Suitable acids include linear, cyclic or aromatic carboxylic or sulphonic acids.

By "precursor" is meant any group that can be hydrolysed to form a carboxylic acid or sulphonic acid or its conjugate base. Suitable precursors include esters, amides and anhydrides of carboxylic or sulphonic acids, with esters and anhydrides being preferred. Most preferred precursors are esters and anhydrides of unsaturated carboxylic acids. Preferably, the precursor compound is non-polymeric.

The formulations preferably comprise unsaturated carboxylic or sulphonic acids, or salts thereof.

Carboxylic acids and their salts and precursors are preferred.

Preferred salts of the unsaturated acid are alkali metal salts, and alkaline earth metal salts. Preferably, alkali metal salts are used. Preferred alkali metals are sodium and potassium.

In one preferred embodiment, the acids are unsaturated cyclic carboxylic acids. Most preferred are unsaturated cyclic monocarboxylic acids.

The unsaturated cyclic acid, salt or precursor thereof may be an aromatic acid, salt or precursor thereof. Suitable aromatic groups include five membered heteroaromatic groups such as furyl, pyrrolyl, and thienyl; six membered aromatic and heteroaromatic groups such as phenyl, pyridyl, pyrazinyl, pyrimidinyl, and pyridazinyl; 9 membered heteroaromatic groups such as indolyl, isoindolyl, and benzimidazyl; and 10 membered aromatic and heteroaromatic groups such as naphthyl, quinolyl, and isoquinolyl. Preferred aromatic or heteroaromatic groups are furyl, pyrrolyl, thienyl, pyridyl, phenyl and naphthyl. Most preferred is phenyl.

Preferred aromatic acids are represented by the general formula (IV)

(IV)

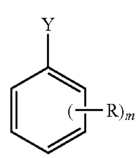

wherein Y denotes $CO_2$14 or $SO_3M$;

each R independently denotes $C_1$-$C_4$ alkyl, OH, OMe, OEt, $NH_2$, $NMe_2$, $CO_2M$ or halogen, wherein two R groups may optionally form naphthyl;

M denotes H, K or Na;

and m denotes 0 to 5.

Preferably, R denotes $C_1$-$C_4$ alkyl, $CO_2H$ or OH and m denotes 0 to 2. More preferably, R denotes OH and m denotes 0 or 1.

Preferred aromatic acids and salts are benzoic acid, sodium benzoate, salicyclic acid, sodium salicyclate, phthalic acid (or phthalic anhydride), benzene sulphonic acid, p-toluene sulphonic acid, sodium tosylate, phenol sulphonic acid, naphthanoic acid, and naphthalene sulphonic acid. Particularly preferred aromatic acids are benzoic acid, sodium benzoate, salicyclic acid, and sodium salicyclate, with alkali metal salts of benzoic acid and particularly sodium benzoate being the most preferred.

Alternatively, or in addition to aromatic acids, the unsaturated cyclic acid, salt or precursor thereof may be an unsaturated polycyclic acid. Preferred unsaturated polycyclic acids are resin acids. Resin acids are produced by parenchymatous epithelial cells that surround the resin ducts in trees from temperate coniferous forests. Typically, the compositions of the present invention will use a mixture of resin acids in the form of rosin, or other naturally derived resins.

Rosin (also termed rosin acid) is a solid form of resin produced by heating fresh liquid resin to vaporise the volatile liquid terpene components. Rosin consists mainly of abietic acid, and in a higher concentration than the level found in resin.

A further derivative containing resin acids that may be used in the composition of the present invention is tall oil. Tall oil (also called liquid rosin) is obtained as a by-product of the Kraft process of wood pulp manufacture. Crude tall oil contains rosin, resin acids (mainly abietic acid and its isomers), fatty acids (mainly palmitic, oleic and linoleic acids) fatty alcohols, sterols and alkyl hydrocarbon derivatives.

Preferred resin acids are abietic-type acids such as abietic acid, neoabietic acid, dehydroabietic acid, and palustric acid, as well as pimaric-type acids such as pimaric acid, levopimaric acid, isopimaric acid. Most preferred are abietic acid, sodium abietate, pimaric acid and sodium pimarate.

As an alternative, or in addition to, the unsaturated cyclic acid, the unsaturated acid component may comprise a linear unsaturated acid, salt or precursor thereof. By "linear" is meant a branched or unbranched alkenyl chain. However, unbranched alkenyl chains are preferred. The linear unsaturated acid may be a mono or a dicarboxylic or sulphonic acid, wherein the acid groups are at the end of the alkenyl chain. Carboxylic acids are preferred, with monocarboxylic acids, salts or precursors thereof being the most preferred.

The linear unsaturated acid may be of any length, although preferably the unsaturated acid has at least 4 carbon atoms, more preferably from 6 to 22 carbon atoms, more preferably from 6 to 18 carbon atoms, most preferably from 6 to 8 carbon atoms.

Preferred linear unsaturated monocarboxylic acids include sorbic acid, myristoleic acid, palmitoleic acid, oleic acid, elaidic acid, linoleic acid, α-linolenic acid, arachidonic acid, eicosapentaenoic acid, euric acid, and docosahexanoic acid. Preferred unsaturated monocarboxylic acids include sorbic acid, myristoleic acid, palmitoleic acid, oleic acid, elaidic acid, linoleic acid, and α-linolenic acid. Preferably, the linear unsaturated monocarboxylic acid is an ω-6 fatty acid.

In a preferred embodiment, the linear unsaturated carboxylic or sulphonic acids are alkali metal salts and esters. Preferred alkali metal salts are sodium and potassium.

In a preferred embodiment, the unsaturated acid precursor is a glycerol ester of an unsaturated fatty carboxylic acid.

Especially preferred unsaturated monocarboxylic acids include sorbic acid and oleic acid and salts thereof, with sorbic acid being preferred. Alkali metal salts of sorbic acid are particularly preferred, with the most preferred being sodium sorbate and potassium sorbate.

Preferred linear unsaturated dicarboxylic acid include fumaric acid, maleic acid (or maleic anhydride). Most preferred is fumaric acid.

These linear unsaturated carboxylic acids may be present in the composition of the present invention as pure acids, or as part of a mixture of different acids. Optionally, these mixtures may be in the form of a natural oil such as tall oil, linseed oil, castor oil, corn oil, coconut oil, olive oil or fish oils such as cod liver oil. Tall oil and linseed oil are particularly preferred.

The acids are typically relatively weak, i.e. with a pKa above 4.0.

Thus, it is particularly preferred for the unsaturated acid to be selected from the group consisting of resin acids, alkali metal salts of salicyclic acid, for example sodium salicyclate and potassium salicyclate, alkali metal salts of benzoic acid, for example sodium benzoate and potassium benzoate, and alkali metal salts or sorbic acid, for example sodium sorbate and potassium sorbate.

The formulations of the present invention comprise one or more azole compounds, i.e. a compound comprising an azole group. The azole compound may be an imidazole or a 1,2,4-triazole and is preferably represented by the general formula (V)

(V)

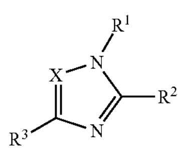

wherein

X denotes $CR^4$ or N;

$R^1$ denotes hydrogen or a linear, branched, cyclic, aromatic or any combination thereof, saturated or unsaturated, substituted or unsubstituted $C_1$ to $C_{40}$ group wherein any of the carbon atoms other than those bound to the nitrogen atom shown in formula (IV) may be replaced with an optionally substituted hetero atom;

$R^1$ denotes hydrogen, $C_1$-$C_8$ alkyl, $C_2$-$C_8$ alkenyl, $C_6$-$C_{10}$ aromatic, $C_5$-$C_{10}$ heteroaromatic or $C_1$-$C_4$ alkyl carbamate;

$R^3$ and $R^4$ denote hydrogen; or together $R^3$ and $R^4$ may provide a benzimidazole group.

The imidazole compound incorporates a five-membered diunsaturated ring composed of three carbon atoms and two nitrogen atoms at non-adjacent positions. The imidazole compound may be a benzimidazole. Preferred compounds include thiabendazole, imazalil, carbendazim and prochloraz.

The 1,2,4-triazole compound incorporates a five-membered diunsaturated ring composed of three nitrogen atoms and two carbon atoms at non-adjacent positions.

Preferred triazole compounds include a triazole compound selected from compounds of formula (VI):

(VI)

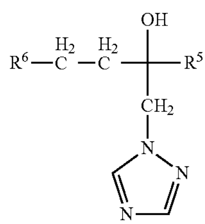

wherein $R^5$ represents a branched or straight chain $C_{1-5}$ alkyl group (e.g. t-butyl) and $R^6$ represents a phenyl group optionally substituted by one or more substituents selected from halogen (e.g. chlorine, fluorine or bromine) atoms or $C_{1-3}$ alkyl (e.g. methyl), $C_{1-3}$ alkoxy (e.g. methoxy), phenyl or nitro groups.

Alternatively, the triazole compound is advantageously selected from compounds of formula (VII):

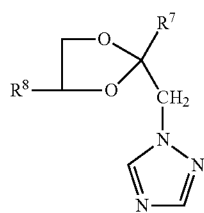

wherein $R^7$ is as defined for $R^6$ above and $R^8$ represents a hydrogen atom or a branched or straight chain $C_{1-5}$ alkyl group (e.g. n-propyl).

Particularly preferred triazoles include, but are not limited to, triadimefon, triadimenol, triazbutil, propiconazole, cyproconazole, difenoconazole, fluquinconazole, tebuconazole, flusilazole, uniconazole, diniconazole, bitertanol, hexaconazole, azaconazole, flutriafol, epoxyconazole, tetraconazole, penconazole, and mixtures thereof.

Most preferred triazoles are propiconazole, azaconazole, hexaconazole, tebuconazole, cyproconazole, triadimefon and mixtures thereof.

The compositions typically comprise one or more further active ingredients. Preferred examples of additional active ingredients are quaternary ammonium compounds. A further preferred active ingredient is an amine oxide. Suitable quaternary ammonium compounds and amine oxides that may be used in the compositions of the present invention are described in for example WO2007/135435. Preferred quaternary ammonium compounds are trimethyl alkyl quaternary ammonium compounds such as cocotrimethyl ammonium chloride; dialkyldimethyl quaternary ammonium compounds such as didecyl dimethyl ammonium chloride, didecyl dimethyl ammonium carbonate, didecyl dimethyl ammonium bicarbonate, dioctyl dimethyl ammonium chloride and octyl decyl dimethyl ammonium chloride, or mixtures thereof; alkyl dimethyl or diethyl benzyl ammonium salts such as benzalkonium chloride and benzalkonium hydroxide; polyethoxylated quaternary ammonium compounds such as N,N-didecyl-N-methyl-poly(oxyethyl)ammonium propionate (Bardap 26) or N,N-didecyl-N-methyl-poly(oxyethyl)ammonium lactate; and N-substituted pyridinium compounds such as cetyl pyridinium chloride. Preferred amine oxides include alkyldimethylamine oxides such as $C_{10}$ alkyldimethylamine oxide, $C_{10}$-$C_{14}$ alkyldimethylamine oxide, $C_{12}$-$C_{16}$ alkyldimethylamine oxide, $C_{16}$-$C_{18}$ alkyldimethylamine oxide, and mixtures thereof. Particularly preferred are $C_{12}$-$C_{14}$ alkyldimethylamine oxides, with $C_{12}$ alkyldimethylamine oxide being the most preferred.

In an alternative, but also preferred class of formulations, amine oxide is not included in the formulation. Alternatively, if an amine oxide is present, it is not included in combination with either a betaine, a quaternary ammonium compound or a dimethyl alkyl amine.

The compositions according to the invention may additionally comprise other active ingredients such as termiticides, insecticides, bacteriocides and other fungicides. Suitable additional fungicides would be apparent to one skilled in the art and will vary according to the application. In particular, additional fungicides which extend the spectrum of activity of the formulation may be chosen, such as fungicides active against bluestain fungi, white rots, brown rots, dry rots and moulds. Suitable additional fungicides include for example, dichlofluanid, acypetacs, including copper and zinc salts, isothiazolones, tolyfluanid, chlorothanonil, fenpropimorph, borates, guazatine and salts thereof, oxathiazines such as bethoxazin, TCMTB, MBT, PCP and its salts, N-(3-aminopropyl)-N-dodecylpropane-1,3-diamine, Dazomet, (E)-1-(2-chloro-1,3-thiazol-5-ylmethyl-2-nitroguanadine, polyhexamethylenebiguanide hydrochloride (PHMB), as well as metal compounds such as copper, Cu-oxide, copper naphthenate, copper carbonate, copper oxine, copper hydroxide, copper dihydroxide, Cu-HDO, potassium-HDO, also iron and zinc and salts, compounds and soaps thereof. However, preferred compositions of the invention are free of biocidal metal ions, particularly free of copper.

Suitable insecticides would also be apparent to the skilled man depending upon the intended application, and include, for example, chlorpyrifos, cypermethrin, fenvalerate, fenoxycarb, fipronil, farox, tetramethrin, isofenphos, permethrin, silafluofen, deltamethrin, bifenthrin, cyfluthrin, chlorfenapyr, thiachloprid; etofenprox, chlothianidin, thiamethoxam and imidacloprid, and benzoylureas such as lufenuron, hexaflumuron and flufenoxuron and in particular, flurox.

The compositions according to the invention may additionally comprise other components which may act to improve the characteristics of the wood treated with these biocides. Such compounds could include water repellents based on waxes, silicones and polysiloxanes, latex, fluorocarbon, organic carboxylate/metals, paper sizing agents or amine oxides, or combinations thereof; resins or crosslinking agents based on alkyds, acrylics, polyurethanes, formaldehydes, dimethylol, and epichlorohydrin or combinations thereof. Oils may also be used as may UV absorbers, corrosion inhibitors, penetrating aids including glycols, bactericides for example PHMB, colouring agents, antioxidants, metal chelators especially iron chelators, optical brightening agents, defoamers, pH buffers or other stabilisers. Preferred coadditives include PHMB and ethoxylated amines, such as those described in WO2007/026008. Ethoduomeen T/13® is a particularly preferred ethoxylated amine.

The inventors have shown that the efficacy of the formulations described is surprisingly greater than would be expected based on an additive effect. Therefore synergy is taking place. Thus, preferred compositions comprise an azole and, in proportions which are synergistic as between the two components, a haloalkylnyl compound and an unsaturated carboxylic or sulphonic acid, salt or precursor thereof.

It has been found that in some embodiments using complex mixtures of naturally occurring fatty acids, the presence of large amounts of saturated fatty acids can reduce the synergistic effect of the unsaturated acids. Therefore, in a preferred embodiment, the fatty acid component contains less than 40 weight percent saturated carboxylic acids, preferably, less than 25 weight percent saturated carboxylic acids, more preferably less than 10 weight percent saturated carboxylic acids, most preferred is less than 5 weight percent weight saturated carboxylic acids.

In relation to the total formulation, the formulation of the present invention preferably contains less that 2 weight percent saturated fatty acid, more preferably less than 1 weight percent saturated fatty acid, more preferably less than 0.5 weight percent saturated fatty acid, more preferably less than 0.2 weight percent saturated fatty acid, most preferred is less than 0.1 weight percent saturated fatty acid. In this context, a saturated fatty acid is a carboxylic acid having an alkyl group with from 6 to 24 carbon atoms.

Particularly effective ratios of unsaturated acid, salt or precursor thereof to haloalkylnyl compound are 1:5 to 50:1, preferably 1:2 to 30:1, more preferably 1:1 to 25:1, more preferably 2:1 to 15:1, most preferably 2:1 to 10:1.

The ratio of unsaturated acid to haloalkylnyl will vary depending upon the type of acid present in the composition. In general, it has been found that the amount of acid present should be greater than the amount of haloalkylnyl (in weight percent). However, some of the naturally occurring cyclic acids such as rosin have relatively poor solubility. The compositions of the invention typically comprise about 1-2 weight percent haloalkylnyl compound. If it is not possible to dissolve an excess of unsaturated acid in the composition, then the unsaturated acid is typically added to form a saturated or near saturated solution of the acid.

All of the above ratios refer to weight percent as a percentage of the total weight of the composition. Thus, a ratio of 1:1 will refer to two components being present in equal weight percents in a composition.

Thus, especially preferred formulations according to the present invention comprise benzoic acid (or sodium benzoate), sorbic acid (or potassium sorbate), or rosin; a triazole compound; and IPBC; all as defined above and preferably at the ratios specified above.

The concentration of the formulation required for preservative treatment depends on the ratio of particular active agents selected, the method of treatment employed, the timber species, the level of protection required and the nature and quantity of any other biocides present. The amounts necessary can be determined readily by one skilled in the art. In concentrate form the wood treatment composition will typically comprise as active ingredients 0.1-10%, preferably 0.2-5%, e.g. 0.2-2% w/w of azole, and 0.1-10%, preferably 0.2-5%, e.g. 0.5-3% w/w haloalkylnyl compound. Typically these concentrates will be diluted prior to application to the wood. Dilution will preferably be with water, e.g. at a ratio, water: concentrate v/v of 15:1 to 250:1 e.g. 75:1 to 150:1. The appropriate dilution level can be determined by one skilled in the art dependent upon cost, the type of wood to be treated, environmental conditions and the length of time protection is required.

In a further aspect, the invention provides a method of preserving wood or other cellulosic substrates which comprises applying to the wood or other cellulosic substrate a composition of the invention as described above or applying the individual components to the wood/substrate such that the wood/substrate effectively receives a composition as described. Preferably, the invention provides a method of preventing sapstain formation on wood or other cellulosic material which comprises applying to the wood or other cellulosic substrate a composition of the invention as described above or applying the individual components to the wood/substrate such that the wood/substrate effectively receives a composition as described.

Thus, the invention also provides a method of maintaining the visual appearance of wood or other substrates which comprises applying to the wood or other cellulosic substrate a composition of the invention as described above or applying the individual components to the wood/substrate such that the wood/substrate effectively receives a composition as described. The Examples disclose methods of assessing visual appearance.

Types of wood which can benefit from treatment with the formulations of the invention include sawn timber, logs, glulam, plywood, laminated veneer lumber, wood based composite products such as oriented strandboard, medium density fibreboard, fibreboard, hardboard and particle board.

It will be understood that "wood" in the context of this invention does not encompass living trees or other plants.

Other materials which can benefit from treatment with the formulations of the invention are lignocellulosic substrates, wood plastic composites, cardboard and cardboard faced building products such as plasterboard, and cellulosic material such as cotton. Also, leather, textile materials and even synthetic fibres, hessian, rope and cordage as well as composite wood materials. For convenience, the invention is described with reference to the treatment of wood but it will be appreciated that other materials may be treated analogously. Preferably, though not exclusively, the formulations are applied to sawn timber, logs or laminated veneer lumber. Most preferably, the formulations are applied to unseasoned timber.

Conveniently, the compositions of the present invention are applied as a liquid composition. They may also be applied as a solid implant or paste. Preferably, the compositions are applied as a liquid composition, e.g. in the form of an emulsion made up of solubilised liquid droplets. These emulsions do not contain any biocides in a solid, particulate form. Preferably, the emulsions are in the form of a micro-emulsion. The person skilled in the art of making emulsions knows how to make an emulsion according to the invention by the use of suitable solvents and emulsifying agents.

Preferably, when applied in liquid form, this is in an aqueous solution, but one or more organic solvents or a mixture of water and an organic solvent could also be used. Suitable organic solvents include both aromatic and aliphatic hydrocarbon solvents such as white spirit, petroleum distillate, kerosene, diesel oils and naphthas. Also, benzyl alcohol, 2-phenoxy ethanol, methyl carbitol, propylene carbonate, benzyl benzoate, ethyl lactate and 2-ethyl hexyl lactate.

The application of these compositions may be by one or more of dipping, deluging, spraying, brushing or other surface coating means or by impregnation methods, e.g. high pressure or double vacuum impregnation into the body of the wood or other material, all being techniques well known to the man skilled in the art. Impregnation under pressure is particularly advantageous when the substrate is wood or a wood composite material which is made to become wet during its life, for example, wood for window frames, timber used above ground in exposed environments such as decking and timber used in ground contact or fresh water or salt water environments.

Substrates made of wood or cellulosic material which have been treated with a composition or by a method according to the invention as described herein, comprise further aspects of the present invention. Additionally, substrates made of wood or other cellulosic material comprising a composition according to the invention comprise a further aspect of the present invention.

A further aspect of the present invention is the use of compositions of the present invention in the treatment or, preservation of wood or other cellulosic substrates. Preferably, the invention provides the use of compositions of the present invention in the prevention of sapstain, particularly in the prevention of sapstain on freshly felled timber.

Preferably, the compositions are applied to timber components before they are used but they can also be used remedially as a curative action in preventing continued wood defacement.

In yet a further aspect, the invention provides a method of making an antisapstain composition which comprises admixing a haloalkynyl compound, an azole, and an unsaturated carboxylic or sulphonic acid, salt or precursor thereof. Preferred embodiments discussed above in relation to other aspects of the invention apply mutatis mutandis and thus the above three components may be further combined with one or more of a quaternary ammonium compound, and amine oxide etc.

The invention will be further described with reference to the following non-limiting Examples and Figures.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1 is a drawing of the decking/cladding assembly used in Example 1.

FIG. 2 is a photograph of wood treated with formulation II-2 after exposure for 25 weeks.

FIG. 3 is a photograph of wood treated with formulation II-14 after exposure for 25 weeks.

FIG. 4 is a photograph of wood treated with formulation II-19 after exposure for 25 weeks.

FIG. 5 is a photograph of wood treated with formulation II-24 after exposure for 25 weeks.

FIG. 6 is a photograph of wood treated with formulation II-1 after exposure for 25 weeks.

FIG. 7 is a photograph of wood treated with formulation II-16 after exposure for 25 weeks.

FIG. 8 is a photograph of wood treated with formulation II-27 after exposure for 25 weeks.

FIG. 9 is a photograph of wood treated with formulation II-32 after exposure for 25 weeks.

FIG. 10 is a photograph of wood treated with formulation II-33 after exposure for 25 weeks.

FIG. 11 is a photograph of wood treated with formulation II-34 after exposure for 25 weeks.

FIG. 12 is a photograph of wood treated with formulation II-35 after exposure for 25 weeks.

FIG. 13 is a photograph of wood treated with formulation II-36 after exposure for 25 weeks.

EXAMPLES

Example 1

A field trial was initiated in which a number of formulations were investigated for their ability to prolong the period which treated timber could be maintained in a stain and mould free condition.

The formulations were prepared by adding all of the water insoluble ingredients (e.g. azoles, IPBC, any insoluble acids etc.) to the solvent (Dowanol DPM®) and stirring until fully dissolved. The surfactant was then stirred in and water added. Any water soluble additives (e.g. sodium benzoate) were added last.

The formulations used in the test were as follows (including their dilution levels when applied to wood):

Formulation I-1 (Comparative)

| | |
|---|---|
| Dowanol DPM ® | 5.01 |
| Tebuoconazole (97%) | 0.50 |
| IPBC (98%) | 0.50 |
| Propiconazole (50%) | 0.50 |
| Dehscofix CO130F ® (40M ethoxylate castor oil surfactant) | 4.99 |
| Water | 88.50 |

Diluted to 3.33%

Formulation I-2 (Comparative)

| | |
|---|---|
| Dowanol DPM ® (Glycol Ether Solvent) | 8.99 |
| Tebuoconazole (97%) | 1 |
| Propiconazole (50%) | 1.03 |
| Dehscofix CO130F ® (40M ethoxylate castor oil surfactant) | 11.34 |
| Tetra-Sodium EDTA (45%) | 1.5 |
| Sodium Benzoate | 22.5 |
| Water | 53.64 |

Diluted to 1.17%

Formulation I-3 (Comparative)

| | |
|---|---|
| Tebuoconazole (97%) | 0.33 |
| Propiconazole (50%) | 0.33 |
| Uradil AZ543 ® (Water Soluble Alkyd Resin) | 15 |

-continued

| | |
|---|---|
| Carboquat ® (didecyldimethylammonium carbonate) | 10 |
| Sodium Benzoate | 22.5 |
| Water | 51.84 |

Diluted to 1.33%

Formulation I-4

| | |
|---|---|
| Dowanol DPM ® (Glycol Ether Solvent) | 8.99 |
| Tebuconazole (97%) | 1 |
| IPBC (98%) | 1.2 |
| Propiconazole (50%) | 1.04 |
| Dehscofix CO130F ® (40M ethoxylate castor oil surfactant) | 11.24 |
| Tetra-Sodium EDTA (45%) | 1.5 |
| Sodium Benzoate | 22.5 |
| Water | 52.53 |

Diluted to 1.02%

Formulation I-5

| | |
|---|---|
| Dowanol DPM ® (Glycol Ether Solvent) | 8.99 |
| Tebuconazole (97%) | 0.75 |
| IPBC (98%) | 1.2 |
| Triadamedon (97%) | 0.75 |
| Dehscofix CO130F ® (40M ethoxylate castor oil surfactant) | 11.24 |
| Tetra-Sodium EDTA (45%) | 1.5 |
| Sodium Benzoate | 22.5 |
| Water | 53.07 |

Diluted to 1.17%

Formulation I-6 (Comparative)

| | |
|---|---|
| Dowanol DPM ® (Glycol Ether Solvent) | 4.99 |
| Tebuconazole (97%) | 0.51 |
| Propiconazole (50%) | 0.51 |
| Dehscofix CO130F ® (40M ethoxylate castor oil surfactant) | 5.00 |
| Rosin Acid Emulsion (50% Rosin Acid) | 2.52 |
| Water | 86.48 |

Diluted to 3.33%

Formulation I-7

| | |
|---|---|
| Dowanol DPM ® (Glycol Ether Solvent) | 5.00 |
| Tebuconazole (97%) | 0.51 |
| IPBC (98%) | 0.51 |
| Propiconazole (50%) | 0.51 |
| Dehscofix CO130F ® (40M ethoxylate castor oil surfactant) | 4.99 |
| Rosin Acid Emulsion (50% Rosin Acid) | 2.52 |
| Water | 85.96 |

Diluted to 3.33%

Formulation I-8 (Comparative)

| | |
|---|---|
| Dowanol DPM ® (Glycol Ether Solvent) | 8.99 |
| Tebuconazole (97%) | 1 |
| IPBC (98%) | 1.2 |
| Propiconazole (50%) | 1.04 |
| Dehscofix CO130F ® (40M ethoxylate castor oil surfactant) | 11.24 |
| Tetra-Sodium EDTA (45%) | 1.5 |
| Sodium Nitrite | 18.5 |
| Water | 56.53 |

Diluted to 1.17%

Formulation I-9 (Comparative)

| | |
|---|---|
| Dowanol DPM ® (Glycol Ether Solvent) | 5.00 |
| Tebuoconazole (97%) | 0.35 |
| IPBC (98%) | 0.39 |
| Propiconazole (50%) | 0.66 |
| Dehscofix CO130F ® (40M ethoxylate castor oil surfactant) | 5.05 |
| Styrene-Acrylic Resin | 9.99 |
| Water | 78.56 |

Diluted to 3.33%

Formulation I-10 (Comparative)

| | |
|---|---|
| Dowanol DPM ® (Glycol Ether Solvent) | 4.98 |
| Tebuoconazole (97%) | 0.35 |
| IPBC (98%) | 0.39 |
| Propiconazole (50%) | 0.66 |
| Dehscofix CO130F ® (40M ethoxylate castor oil surfactant) | 4.98 |
| Iron Oxide Pigment | 0.50 |
| Water | 88.15 |

Diluted to 3.33%

Formulation I-11 (Comparative)

| | |
|---|---|
| Dowanol DPM ® (Glycol Ether Solvent) | 4.98 |
| Tebuoconazole (97%) | 0.35 |
| IPBC (98%) | 0.39 |
| Propiconazole (50%) | 0.66 |
| Uradil AZ543 ® (Water Soluble Alkyd Resin) | 4.98 |
| Anilazine | 0.35 |
| Water | 88.15 |

Diluted to 3.33%

Formulation I-12 (Comparative)

| | |
|---|---|
| Dowanol DPM ® (Glycol Ether Solvent) | 4.97 |
| Tebuoconazole (97%) | 0.50 |
| IPBC (98%) | 0.51 |
| Propiconazole (50%) | 0.51 |
| Dehscofix CO130F ® (40M ethoxylate castor oil surfactant) | 4.96 |
| HAL* (4-Hydroxy-2,2,6,6-tetramethylpiperidinoxyl) | 0.29 |
| Water | 88.27 |

Diluted to 3.33%

*HAL = Hindered amine light scavenger

Formulation I-13 (Comparative)

| | |
|---|---|
| Dowanol DPM ® (Glycol Ether Solvent) | 4.98 |
| Tebuoconazole (97%) | 0.35 |
| IPBC (98%) | 0.39 |
| Propiconazole (50%) | 0.66 |
| Uradil AZ543 ® (Water Soluble Alkyd Resin) | 4.98 |
| Titanium Dioxide Pigment | 0.50 |
| Water | 88.15 |

Diluted to 3.33%

Formulation I-14 (Comparative)

| | |
|---|---|
| Dowanol DPM ® (Glycol Ether Solvent) | 4.61 |
| Tebuoconazole (97%) | 0.47 |
| IPBC (98%) | 0.47 |
| Propiconazole (50%) | 0.48 |

-continued

| | |
|---|---|
| Dehscofix CO130F ® (40M ethoxylate castor oil surfactant) | 4.61 |
| Vantocil IB ® (20% PHMB) | 11.08 |
| Water | 78.27 |

Diluted to 3.33%

Formulation I-15 (Comparative)

| | |
|---|---|
| Dowanol DPM ® (Glycol Ether Solvent) | 4.95 |
| Tebuoconazole (97%) | 0.50 |
| IPBC (98%) | 0.50 |
| Barlene 12C (amine) | 2.39 |
| Propionic Acid | 1.48 |
| Propiconazole (50%) | 0.50 |
| Dehscofix CO130F ® (40M ethoxylate castor oil surfactant) | 4.95 |
| Water | 84.72 |

Diluted to 3.33%

Formulation I-16 (Comparative)

| | |
|---|---|
| Dowanol DPM ® (Glycol Ether Solvent) | 5.00 |
| Tebuoconazole (97%) | 0.35 |
| Propiconazole (50%) | 0.66 |
| Uradil AZ543 ® (Water Soluble Alkyd Resin) | 5.00 |
| Ethoduomeen T13 ® | 1.34 |
| Water | 87.65 |

Diluted to 3.33%

The test formulations were evaluated using small pine blocks and pine decking/cladding structures.

The small block test substrates consisted of planed timber blocks of dimension 135×70×25 mm which were machined from Scots Pine (pinus sylvestris). The upper face of each block consisted entirely of sapwood. Five duplicate blocks were treated with each of the formulations.

The blocks were treated using vacuum-pressure impregnation with initial wet vacuum of 650 mm Hg vacuum applied for a period of 30 minutes followed by a pressure cycle of 12 $kg/cm^2$ also for 30 minutes. After treatment the blocks were allowed to dry slowly on the bench for one week prior to exposure.

For exposure the blocks were mounted horizontally on untreated pine racks at ground level on a gravel surface for natural weathering exposure.

The decking/cladding structure for natural weathering exposure were also machined from Scots Pine. The dimensions of each of the section types used in construction of each structure are shown in Table 1 below. For each treatment solution, 6 deck sections, 4 cladding sections, 3 joists, and 2 batons were treated. The end of each section was then sealed with a nitrocellulose lacquer to reduce the risk of solution penetration occurring only through the end grain rather than laterally. This ensured that large pieces of timber received the same level of formulation across their entire length. The structures were assembled as per FIG. 1.

TABLE 1

Timber section dimensions for pine decking/cladding structure

| Pine | Width mm | Depth mm | Length mm |
|---|---|---|---|
| Decking | 120 | 30 | 730 |
| Cladding | 125 | 15 | 730 |
| Joists | 100 | 50 | 530 |
| Batons | 50 | 35 | 700 |

The treated timber were then exposed above ground in an in-service situation defined as Hazard Class 3 (uncoated) by EN355. The samples were periodically inspected to determine if stain and/or mould had begun to grow. The stain and mould free period of each of the formulations (i.e. the number of months that the sample was graded 0 according to the EN152:1988 standard) is summarised in Table 2.

TABLE 2

Stain and mould free period of timber treated with formulations I-1 to I-16

| Form. | Fungicides | Co-additive | Stain and mould free period |
|---|---|---|---|
| I-1* | IPBC/Teb/Prop | | 2 months |
| I-2* | Teb/Prop | Na Benzoate | 2 months |
| I-3* | DDAC/Teb/Prop | Na Benzoate | 1 month |
| I-4 | IPBC/Teb/Prop | Na Benzoate | 9 months |
| I-5 | IPBC/Teb/Tria | Na Benzoate | 9 months |
| I-6* | Teb/Prop | Rosin | 2 months |
| I-7 | IPBC/Teb/Prop | Rosin | 7 months |
| I-8* | IPBC/Teb/Prop | Na Nitrite | 1 month |
| I-9* | IPBC/Teb/Prop | Styrene | 1 month |
| I-10* | IPBC/Teb/Prop | Iron Oxide | 3 months |
| I-11* | IPBC/Teb/Prop | UV Absorber | 3 months |
| I-12* | IPBC/Teb/Prop | UV Absorber | 3 months |
| I-13* | IPBC/Teb/Prop | $TiO_2$ | 3 months |
| I-14* | IPBC/Teb/Prop | Anti Microb. | 3 months |
| I-15* | IPBC/Teb/Prop | Anti Microb. | 3 months |
| I-16* | IPBC/Teb/Prop | Diamine | 2 months |

(*denotes comparative example).

The data for formulations I-1 to I-5 show that timber treated with a combination of IPBC/azole/benzoate has a stain and mould free period 7 months longer than timber treated with the combination of IPBC/azole or azole/benzoate alone. Furthermore, the improved resistance is not present in formulation I-3, which contains DDACarbonate (a known fungicide and adjuvant) in place of IPBC. The levels of each of the active fungicides present in each of the compositions is the same. Therefore, synergy is present in the combination of IPBC/azole/benzoate.

The data for formulations I-6 and I-7 show that timber treated with a combination of IPBC/azole/rosin has a stain and mould free period 5 months longer than timber treated with azole/rosin alone. Therefore, synergy is present in the IPBC/azole/rosin combination.

Sodium benzoate is a known corrosion inhibitor. However, formulation I-8 contains sodium nitrite which is also known to have corrosion inhibiting properties. The timber treated with formulation I-8 showed poor resistance to stain and mould.

Including co-additives in the formulation to help prevent IPBC degradation does not significantly increase the stain and mould free period. For example, the presence of water repellent additives (formulation I-9), UV absorbers or metal oxide particles which either absorb or scatter light to prevent photodegredation (formulations I-10 to I-13), or antimicrobials (formulations I-14 and I-15) in the compositions used to treat the timber did not prolong the stain and mould free period. The inclusion of adjuvants such as amine proprionate or Ethoduomeen T13® (an ethoxylated diamine) (formulations I-15 and I-16), which could be expected to facilitate azole/IPBC penetration, also does not prolong the stain and mould free period.

Example 2

A trial was conducted in which a number of formulations were investigated for their ability to prevent blue stain growth.

The formulations were prepared by adding all of the water insoluble ingredients (e.g. azoles, IPBC, any insoluble acids etc.) to the solvent (Dowanol PPM®) and stirring until fully dissolved. The surfactant was then stirred in and water added. Any water soluble additives (e.g. sodium benzoate) were added last.

The formulations tested were as follows (with the ingredients listed as weight percent):

Formulation II-1 (Comparative)

| | |
|---|---|
| IPBC (98%) | 1.11 |
| Surfactant | 11.25 |
| Dowanol DPM ® | 8.8 |
| Water | 78.84 |

Formulation II-2 (Comparative)

| | |
|---|---|
| IPBC (98%) | 1.11 |
| Surfactant | 11.25 |
| Dowanol DPM ® | 8.8 |
| Sodium Benzoate | 22.5 |
| Water | 56.34 |

Formulation II-3 (Comparative)

| | |
|---|---|
| IPBC (98%) | 1.11 |
| Surfactant | 30.05 |
| Dowanol DPM ® | 16.6 |
| Abietic Acid | 3.76 |
| Water | 48.48 |

Formulation II-4 (Comparative)

| | |
|---|---|
| Tebuconazole (95%) | 1.5 |
| Surfactant | 11.25 |
| Dowanol DPM ® | 8.8 |
| Water | 78.45 |

Formulation II-5 (Comparative)

| | |
|---|---|
| Propiconazole (50%) | 3 |
| Surfactant | 11.25 |
| Dowanol DPM ® | 8.8 |
| Water | 76.95 |

Formulation II-6 (Comparative)

| | |
|---|---|
| Triadimefon (95%) | 1.5 |
| Surfactant | 11.25 |
| Dowanol DPM ® | 8.8 |
| Water | 78.45 |

Formulation II-7 (Comparative)

| | |
|---|---|
| Imazalil (97.5%) | 1.5 |
| Surfactant | 11.25 |
| Dowanol DPM ® | 8.8 |
| Water | 78.45 |

Formulation II-8 (Comparative)

| | |
|---|---|
| Tebuconazole (95%) | 1 |
| Propiconazole (50%) | 1 |
| Surfactant | 11.25 |
| Dowanol DPM ® | 8.8 |
| Water | 77.95 |

Formulation II-9 (Comparative)

| | |
|---|---|
| Tebuconazole (95%) | 0.75 |
| Triadimefon (95%) | 0.75 |
| Surfactant | 11.25 |
| Dowanol DPM ® | 8.8 |
| Water | 78.45 |

Formulation II-10 (Comparative)

| | |
|---|---|
| Tebuconazole (95%) | 1.5 |
| Surfactant | 11.25 |
| Dowanol DPM ® | 8.8 |
| Sodium Benzoate | 22.5 |
| Water | 55.95 |

Formulation II-11 (Comparative)

| | |
|---|---|
| Propiconazole (50%) | 3 |
| Surfactant | 11.25 |
| Dowanol DPM ® | 8.8 |
| Sodium Benzoate | 22.5 |
| Water | 54.45 |

Formulation II-12 (Comparative)

| | |
|---|---|
| Triadimefon (95%) | 1.5 |
| Surfactant | 11.25 |
| Dowanol DPM ® | 8.8 |
| Sodium Benzoate | 22.5 |
| Water | 55.95 |

Formulation II-13 (Comparative)

| | |
|---|---|
| Imazalil (97.5%) | 1.5 |
| Surfactant | 11.25 |
| Dowanol DPM ® | 8.8 |
| Sodium Benzoate | 22.5 |
| Water | 55.95 |

Formulation II-14 (Comparative)

| | |
|---|---|
| Tebuconazole (95%) | 1 |
| Propiconazole (50%) | 1 |
| Surfactant | 11.25 |
| Dowanol DPM ® | 8.8 |
| Sodium Benzoate | 22.5 |
| Water | 55.45 |

Formulation II-15 (Comparative)

| | |
|---|---|
| Tebuconazole (95%) | 0.75 |
| Triadimefon (95%) | 0.75 |
| Surfactant | 11.25 |
| Dowanol DPM ® | 8.8 |
| Sodium Benzoate | 22.5 |
| Water | 55.95 |

Formulation II-16 (Comparative)

| | |
|---|---|
| IPBC (98%) | 1.11 |
| Propiconazole (50%) | 3 |
| Surfactant | 11.25 |
| Dowanol DPM ® | 8.8 |
| Water | 75.84 |

Formulation II-17 (Comparative)

| | |
|---|---|
| IPBC (98%) | 1.11 |
| Propiconazole (50%) | 3 |
| Surfactant | 11.25 |
| Dowanol DPM ® | 8.8 |
| Water | 75.84 |

Formulation II-18 (Comparative)

| | |
|---|---|
| IPBC (98%) | 1.11 |
| Imazalil (97.5%) | 1.5 |
| Surfactant | 11.25 |
| Dowanol DPM ® | 8.8 |
| Water | 77.34 |

Formulation II-19 (Comparative)

| | |
|---|---|
| IPBC (98%) | 1.11 |
| Tebuconazole (95%) | 1 |
| Propiconazole (50%) | 1 |
| Surfactant | 11.25 |
| Dowanol DPM ® | 8.8 |
| Water | 76.84 |

Formulation II-20 (Comparative)

| | |
|---|---|
| IPBC (98%) | 1.11 |
| Tebuconazole (95%) | 0.75 |
| Triadimefon (95%) | 0.75 |
| Surfactant | 11.25 |
| Dowanol DPM ® | 8.8 |
| Water | 77.34 |

Formulation II-21

| | |
|---|---|
| IPBC (98%) | 1.11 |
| Propiconazole (50%) | 3 |
| Surfactant | 11.25 |
| Dowanol DPM ® | 8.8 |
| Sodium Benzoate | 22.5 |
| Water | 53.34 |

Formulation II-22

| | |
|---|---|
| IPBC (98%) | 1.11 |
| Propiconazole (50%) | 3 |
| Surfactant | 11.25 |
| Dowanol DPM ® | 8.8 |
| Sodium Benzoate | 22.5 |
| Water | 53.34 |

Formulation II-23

| | |
|---|---|
| IPBC (98%) | 1.11 |
| Propiconazole (50%) | 3 |
| Surfactant | 11.25 |
| Dowanol DPM ® | 8.8 |
| Sodium Benzoate | 22.5 |
| Water | 53.34 |

Formulation II-24

| | |
|---|---|
| IPBC (98%) | 1.11 |
| Propiconazole (50%) | 3 |
| Surfactant | 11.25 |
| Dowanol DPM ® | 8.8 |
| Sodium Benzoate | 22.5 |
| Water | 53.34 |

Formulation II-25

| | |
|---|---|
| IPBC (98%) | 1.11 |
| Tebuconazole (95%) | 0.75 |
| Triadimefon (95%) | 0.75 |
| Surfactant | 11.25 |
| Dowanol DPM ® | 8.8 |
| Sodium Benzoate | 22.5 |
| Water | 54.84 |

Formulation II-26

| | |
|---|---|
| IPBC (98%) | 1.11 |
| Tebuconazole (95%) | 1.5 |
| Surfactant | 30.05 |
| Dowanol DPM ® | 16.6 |
| Abietic Acid | 3.76 |
| Water | 46.98 |

Formulation II-27

| | |
|---|---|
| IPBC (98%) | 1.11 |
| Propiconazole (50%) | 3 |
| Surfactant | 30.05 |
| Dowanol DPM ® | 16.6 |
| Abietic Acid | 3.76 |
| Water | 45.48 |

Formulation II-28

| | |
|---|---|
| IPBC (98%) | 1.11 |
| Triadimefon (95%) | 1.5 |
| Surfactant | 30.05 |
| Dowanol DPM ® | 16.6 |
| Abietic Acid | 3.76 |
| Water | 46.98 |

Formulation II-29 (Comparative)

| | |
|---|---|
| Tebuconazole (95%) | 1.5 |
| Surfactant | 30.05 |
| Dowanol DPM ® | 16.6 |
| Abietic Acid | 3.76 |
| Water | 48.09 |

Formulation II-30 (Comparative)

| | |
|---|---|
| Propiconazole (50%) | 3 |
| Surfactant | 30.05 |
| Dowanol DPM ® | 16.6 |
| Abietic Acid | 3.76 |
| Water | 46.59 |

Formulation II-31 (Comparative)

| | |
|---|---|
| Triadimefon (95%) | 1.5 |
| Surfactant | 30.05 |
| Dowanol DPM ® | 16.6 |
| Abietic Acid | 3.76 |
| Water | 48.09 |

Formulation II-32

| | |
|---|---|
| IPBC (98%) | 1.11 |
| Tebuconazole (95%) | 1 |
| Propiconazole (50%) | 1 |
| Surfactant | 30.05 |
| Dowanol DPM ® | 16.6 |

-continued

| | |
|---|---|
| Sodium Salicylate | 3.76 |
| Water | 46.48 |

Formulation II-33

| | |
|---|---|
| IPBC (98%) | 1.11 |
| Tebuconazole (95%) | 1 |
| Propiconazole (50%) | 1 |
| Surfactant | 11.25 |
| Dowanol DPM ® | 8.8 |
| Potassium Sorbate | 22.5 |
| Water | 54.34 |

Formulation II-34

| | |
|---|---|
| IPBC (98%) | 1.11 |
| Tebuconazole (95%) | 1 |
| Propiconazole (50%) | 1 |
| Surfactant | 11.25 |
| Dowanol DPM ® | 8.8 |
| Rosin Acid Emulsion (50%) | 7.57 |
| Water | 69.27 |

Formulation II-35

| | |
|---|---|
| IPBC (98%) | 1.11 |
| Tebuconazole (95%) | 1 |
| Propiconazole (50%) | 1 |
| Surfactant | 28.02 |
| Dowanol DPM ® | 46.1 |
| Sorbic Acid | 3.76 |
| Water | 19.01 |

Formulation II-36

| | |
|---|---|
| IPBC (98%) | 1.11 |
| Tebuconazole (95%) | 1 |
| Propiconazole (50%) | 1 |
| Surfactant | 28.02 |
| Dowanol DPM ® | 46.1 |
| Oleic Acid | 3.76 |
| Water | 19.01 |

The test formulations (diluted to 0.83% with water) were evaluated using small pine blocks, using identical substrate types and conditions to those described in Example 1.

The treated samples were assigned a grade according to the level of blue stain determined (Table 3). The grading system is in accordance with EN152:1988 parts 1 and 2, which is the standard concerning a laboratory method for determination of the protective effectiveness of a wood preservative treatment against blue stain in wood in service.

TABLE 3

Blue Stain Assessment Grades.

| Grade | Blue Stain Level |
|---|---|
| 0 | Not blue stained: no blue stain can be detected visually on the surface. |

TABLE 3-continued

| Blue Stain Assessment Grades. | |
|---|---|
| Grade | Blue Stain Level |
| 1 | Insignificantly blue stained. The surface exhibits only individual small blue stained spots with a largest diameter of 2 mm. |
| 2 | Blue stained: the surface is continuously blue stained up to a maximum of one third of the surface area, or blue stained partially or in streaks up to half the total area. |
| 3 | Strongly blue stained. More than half the surface area is continuously stained or more than half the surface area is partially blue stained. |

The blue stain grading for each of the formulations is shown in Table 4.

TABLE 4

Blue stain gradings (EN152: 1998) of timber treated with formulations II-1 to II-36

| Form | Ingredient 1 | Ingredient 2 | Ingredient 3 | Grade at 25 Weeks |
|---|---|---|---|---|
| Untreated* | | | | 3 |
| II-1* | IPBC | | | 3 |
| II-2* | IPBC | | Na Benzoate | 2 |
| II-3* | IPBC | | Abietic Acid | 2 |
| II-4* | | Tebuconazole | | 3 |
| II-5* | | Propiconazole | | 3 |
| II-6* | | Triadimefon | | 3 |
| II-7* | | Imazalil | | 3 |
| II-8* | | Teb/Prop | | 3 |
| II-9* | | Teb/Tria | | 3 |
| II-10* | | Tebuconazole | Na Benzoate | 3 |
| II-11* | | Propiconazole | Na Benzoate | 3 |
| II-12* | . | Triadimefon | Na Benzoate | 3 |
| II-13* | | Imazalil | Na Benzoate | 3 |
| II-14* | | Teb/Prop | Na Benzoate | 2 |
| II-15* | | Teb/Tria | Na Benzoate | 3 |
| II-16* | IPBC | Propiconazole | | 3 |
| II-17* | IPBC | Triadimefon | | 3 |
| II-18* | IPBC | Imazalil | | 3 |
| II-19* | IPBC | Teb/Prop | | 3 |
| II-20* | IPBC | Teb/Tria | | 3 |
| II-21 | IPBC | Propiconazole | Na Benzoate | 1 |
| II-22 | IPBC | Triadimefon | Na Benzoate | 1 |
| II-23 | IPBC | Imazalil | Na Benzoate | 1 |
| II-24 | IPBC | Teb/Prop | Na Benzoate | 1 |
| II-25 | IPBC | Teb/Tria | Na Benzoate | 1 |
| II-26 | IPBC | Tebuconazole | Abietic Acid | 2 |
| II-27 | IPBC | Propiconazole | Abietic Acid | 2 |
| II-28 | IPBC | Triadimefon | Abietic Acid | 2 |
| II-29* | | Tebuconazole | Abietic Acid | 3 |
| II-30* | | Propiconazole | Abietic Acid | 3 |
| II-31* | | Triadimefon | Abietic Acid | 3 |
| II-32 | IPBC | Teb/Prop | Na salicylate | 2 |
| II-33 | IPBC | Teb/Prop | K Sorbate | 0 |
| II-34 | IPBC | Teb/Prop | Rosin Acid | 0 |
| II-35 | IPBC | Teb/Prop | Sorbic acid | 2 |
| II-36 | IPBC | Teb/Prop | Oleic acid | 2 |

(*denotes comparative example).

Commercially acceptable blue stain levels are considered to be grades 0 and 1 only. The data in Table 4 demonstrate that the majority of the formulations according to the invention meet the commercially acceptable standards. Of the formulations according to the invention that did not achieve grade 0 or 1, the addition of the unsaturated acid was nevertheless found to be an improvement over the composition absent the acid (see formulations II-26 to II-28 as compared to formulations II-29 to II-31; and formulations II-32, II-35 and II-36 as compared to formulation II-19).

It is notable that the grading scheme is not entirely satisfactory, given the lack of an intermediate level between grade 1 (insignificant stain) and grade 2 (stain partially or in streaks up to half the total area). This may explain why a number of the formulations according to the invention fail to meet current commercial standards, despite the fact that the timber boards treated with these compositions show a marked improvement over the relevant control boards.

To aid comparison of the different formulations, photographs of the test samples were taken after 25 weeks' exposure under diffuse daylight (i.e. overcast conditions) using a Fuji FinePix S5700 digital camera. White balance was set to overcast. Automatic exposure was used giving a typical aperture of f/4.0 and 1/160 second exposure. The samples were photographed from a distance of around 60 cm with the camera held perpendicular to the plane of the block surface.

The photographs obtained were then visually compared to reference samples treated with the equivalent IPBC/Azole formulation absent the additive. These visual comparisons were done by systematically comparing side-by-side colour photographs (displayed on a computer screen) of the exposed wood substrates, and rating the aesthetic quality of the substrates treated with the formulation according to the invention compared its respective control substrate absent the unsaturated acid. A rating of very high indicates that no noticeable discolouration of the substrate is observable, while high indicates that only minor staining is present. A rating of moderate indicates that although staining is present, the composition represents a noticeable improvement over the control sample. Table 5 summarises the results from these visual comparisons.

TABLE 5

Results from visual comparison of unsaturated acid containing formulations versus formulation II-19 containing only IPBC/tebuconazole/propiconazole

| Formulation | Unsaturated acid | Anti-Stain Performance Effectiveness |
|---|---|---|
| II-24 | Na Benzoate | Very high |
| II-27* | Abietic acid | Moderate |
| II-32 | Na Salicyclate | High |
| II-33 | K Sorbate | Very high |
| II-34 | Rosin | Very high |
| II-35 | Sorbic acid | High |
| II-36 | Oleic acid | High |

(*denotes the comparison is made with respect to formulation II-16)

FIGS. 2 to 5 show pictures taken after exposure for 25 weeks of the substrates treated with formulations II-2, II-14, II-19 and II-24 respectively. A comparison of these photographs clearly shows that the combination of IPBC, tebuconazole/propiconazole and sodium benzoate shows a marked improvement over formulations that are absent one of these three ingredients. FIG. 6 shows the substrates treated with formulation II-1 (IPBC) after 25 weeks' exposure. Notably, a comparison of FIGS. 2 and 6 shows that sodium benzoate appears to improve the efficacy of IPBC even when an azole is not present, demonstrating that the unsaturated acid serves to stabilise IPBC improving its long term efficacy.

The data in Table 5 indicate that all of the formulations according to the invention except that containing abietic acid can be rated as high or very high anti-stain performance, indicating that the addition of the unsaturated acid greatly increases the resistance to blue stain growth. However, FIGS. 7 and 8 clearly show that even though it was only rated as moderate, abietic acid clearly improves the efficacy of a mixture containing IPBC/tebuconazole.

The pictures of the substrates from the remaining formulations given in Table 5 are shown in FIGS. 9 to 13. As can be seen, the wood treated with formulations II-32, II-33, II-34, II-35, and II-36 all show lower blue stain levels than the control formulation II-19, shown in FIG. 4. In particular, the substrates treated with Formulations II-33 and II-34 show virtually no blue stain, indicating that potassium sorbate and rosin are particularly effective unsaturated acids in the formulations of the present invention.

Example 3

The following formulations within the scope of the invention are also described:

Formulation III-1

| | |
|---|---|
| IPBC (98%) | 1.11 |
| Tebuconazole (95%) | 1.5 |
| Surfactant | 11.25 |
| Solvent | 8.8 |
| Sodium Benzoate | 22.5 |
| Water | 54.84 |

Formulation III-2

| | |
|---|---|
| IPBC (98%) | 1.11 |
| Tebuconazole (95%) | 1 |
| Propiconazole (50%) | 1 |
| Surfactant | 30.05 |
| Solvent | 16.6 |
| Linoleic Acid | 3.76 |
| Water | 46.48 |

Formulation III-3

| | |
|---|---|
| IPBC (98%) | 1.11 |
| Tebuconazole (95%) | 1 |
| Propiconazole (50%) | 1 |
| Surfactant | 28.02 |
| Solvent | 46.1 |
| Fumaric Acid | 3.76 |
| Water | 19.01 |

Formulation III-4

| | |
|---|---|
| $C_{12}$ dimethylamine (100% a.i.) | 10.0% w/w |
| $C_{12}$ amine dipropionate (35% a.i) | 20 |
| IPBC (98% a.i.) | 2.1 |
| Propiconazole (50% a.i.) | 0.8 |
| Dowanol DPM ® | 12 |
| Propionic acid | 3.4 |
| 40 mole ethoxylated castor oil | 10 |
| Sodium benzoate | 5 |
| Defoamer | 0.2 |
| Water to | 100 |

Formulation III-5

| | |
|---|---|
| $C_{12}$ amine dipropionate (35% a.i.) | 20% w/w |
| $C_{12}$ dimethylamine (100% a.i.) | 10 |
| IPBC (98% a.i.) | 2.1 |
| Propiconazole (50% a.i.) | 0.8 |
| Dowanol DPM | 12 |
| Propionic acid | 3.4 |
| 40 mole ethoxylated castor oil | 10 |
| $C_{12}$ amine oxide (30% a.i) | 3.0 |
| Sodium benzoate | 5 |
| Defoamer | 0.2 |
| Water to | 100 |

The invention claimed is:

1. A wood preservative composition for inhibiting discoloration due to mold, sapstain or fungi, the composition comprising:

a haloalkynyl compound selected from the group consisting of 3-iodo-2-propynyl propyl carbamate, 3-iodo-2-propynyl butyl carbamate, 3-iodo-2-propynyl hexyl carbamate, 3-iodo-2-propynyl cyclohexyl carbamate, 3-iodo-2-propynyl phenyl carbamate, and mixtures thereof, a 1,2,4-triazole compound; and an unsaturated carboxylic acid, or a salt thereof, wherein the unsaturated carboxylic acid has at least 4 carbon atoms, and the ratio of the unsaturated carboxylic acid, or salt thereof, to the haloalkynyl compound on a weight to weight basis ranges from 1:1 to 25:1.

2. The composition as defined in claim 1, wherein the halopropynyl compound is 3-iodo-2-propynyl butyl carbamate (IPBC).

3. The composition as defined in claim 1, wherein the unsaturated carboxylic acid, or salt thereof, is an unsaturated cyclic carboxylic acid, or salt thereof.

4. The composition as defined in claim 3, wherein the unsaturated carboxylic acid, or salt thereof, is an aromatic acid, or salt thereof.

5. The composition as defined in claim 4, wherein the aromatic acid is of formula (IV):

(IV)

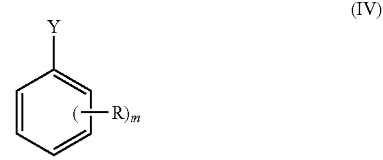

wherein Y denotes $CO_2M$;

each R independently denotes $C_1$-$C_4$ alkyl, OH, OMe, OEt, $NH_2$, $NMe_2$, $CO_2M$ or halogen, wherein two R groups may optionally form naphthyl;

M denotes H, K or Na;

and m denotes 0 to 5.

6. The composition as defined in claim 5, wherein the aromatic acid, or salt thereof, is selected from the group consisting of benzoic acid and sodium benzoate.

7. The composition as defined in claim 3, wherein the cyclic carboxylic acid is a resin acid, or salt thereof.

8. The composition as defined in claim 7, wherein the resin acid, or salt thereof, is selected from the group consisting of abietic acid, sodium abietate, pimaric acid and sodium pimarate.

9. The composition as defined in claim 1, wherein the unsaturated carboxylic acid, or salt thereof, is a linear unsaturated acid, or salt thereof.

10. The composition as defined in claim 1, wherein the unsaturated acid, or salt thereof, is selected from the group consisting of sorbic acid, sodium sorbate, potassium sorbate, myristoleic acid, palmitoleic acid, oleic acid, elaidic acid, linoleic acid, ulinolenic acid, arachidonic acid, eicosapentaenoic acid, euric acid, docosahexanoic acid, fumaric acid, maleic acid, maleic anhydride, and mixtures thereof.

11. The composition as defined in claim 10, wherein the unsaturated acid, or salt thereof, is selected from the group consisting of sorbic acid, sodium sorbate and potassium sorbate.

12. The composition as defined in claim 1, wherein the 1,2,4-triazole compound is a compound selected from the group consisting of formula (VI):

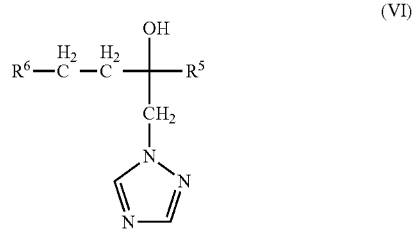

(VI)

wherein $R^5$ represents a branched or straight chain $C_{1-5}$ alkyl group and $R^6$ represents a phenyl group optionally substituted by one or more substituents selected from halogen, $C_{1-3}$ alkyl, $C_{1-3}$ alkoxy, phenyl or nitro;

formula (VII):

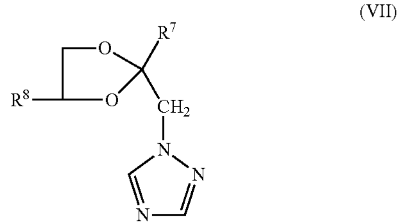

(VII)

wherein $R^7$ is as defined for $R^6$ above and $R^8$ represents a hydrogen atom or a branched or straight chain $C_{1-5}$ alkyl group; and mixtures thereof.

13. The composition as defined in claim 12, wherein the 1,2,4-triazole is selected from the group consisting of triadimefon, triadimenol, triazbutil, propiconazole, cyproconazole, difenoconazole, fluquinconazole, tebuconazole, flusilazole, uniconazole, diniconazole, bitertanol, hexaconazole, azaconazole, flutriafol, epoxyconazole, tetraconazole, penconazole and mixtures thereof.

14. The composition as defined in claim 12, wherein the 1,2,4-triazole is selected from the group consisting of propiconazole, azaconazole, hexaconazole, tebuconazole, cyproconazole, triadimefon and mixtures thereof.

15. The composition as defined in claim 1, wherein the formulation is in a liquid form.

16. The composition as defined in claim 15, wherein the formulation is an emulsion.

17. A method of protecting a substrate formed of wood or cellulosic material which comprises:

applying to the wood or cellulosic substrate a wood preservative composition in an amount to inhibit discoloration due to mold, sapstain or fungi, the wood preservative including a haloalkynyl compound selected from the group consisting of 3-iodo-2-propynyl propyl carbamate, 3-iodo-2-propynyl butyl carbamate, 3-iodo-2-propynyl hexyl carbamate, 3-iodo-2-propynyl cyclohexyl carbamate, 3-iodo-2-propynyl phenyl carbamate, and mixtures thereof, a 1,2,4-triazole compound; and an unsaturated carboxylic acid, or a salt thereof, wherein the unsaturated carboxylic acid has at least 4 carbon atoms, and the ratio of the unsaturated carboxylic acid, or salt thereof, to the haloalkynyl compound on a weight to weight basis ranges from 1:1 to 25:1, or applying the individual components of the wood preservative composition to the wood or cellulosic substrate such that the wood or cellulosic substrate effectively receives the wood preservative in an amount to inhibit discoloration due to mold, sapstain or fungi.

18. A substrate made of wood or cellulosic material treated with an amount of wood preservative to inhibit discoloration due to mold, sapstain or fungi, the wood preservative comprising:

a haloalkynyl compound selected from the group consisting of 3-iodo-2-propynyl propyl carbamate, 3-iodo-2-propynyl butyl carbamate, 3-iodo-2-propynyl hexyl carbamate, 3-iodo-2-propynyl cyclohexyl carbamate, 3-iodo-2-propynyl phenyl carbamate, and mixtures thereof, a 1,2,4-triazole compound; and an unsaturated carboxylic acid, or a salt thereof, wherein the unsaturated carboxylic acid has at least 4 carbon atoms, and the ratio of the unsaturated carboxylic acid, or salt thereof, to the haloalkynyl compound on a weight to weight basis ranges from 1:1 to 25:1.

19. The wood preservative composition as defined in claim 1, wherein the haloalkynyl compound is present in an amount from 0.1 to 10 percent by weight.

20. The wood preservative composition as defined in claim 1, wherein the 1,2,4-triazole compound is present in an amount from 0.1 to 10 percent by weight.

* * * * *